United States Patent

Youssefyeh

[11] 4,355,164
[45] Oct. 19, 1982

[54] PYRIDOTHIENOPYRIDAZINE ANTI-ALLERGY COMPOUNDS

[75] Inventor: Raymond D. Youssefyeh, Tarrytown, N.Y.

[73] Assignee: USV Pharmaceutical Corporation, Tarrytown, N.Y.

[21] Appl. No.: 264,756

[22] Filed: May 18, 1981

[51] Int. Cl.³ .................. C07D 495/14; C07D 495/04
[52] U.S. Cl. ................................. 544/234; 544/233; 546/114; 424/250
[58] Field of Search ............................... 544/233, 234

[56] References Cited
PUBLICATIONS

Shvedov et al., Chem. Abs. 92, 146648p (1979).

Primary Examiner—Mark L. Berch

[57] ABSTRACT

Provided are pyridothienopyridazine compounds of the formula

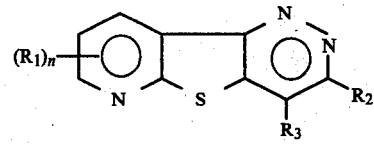

wherein
$R_1$ is alkyl, alkenyl, alkynyl, halogen, nitro, cyano, carboxy, carboxyalkyl, carbalkoxy, alkanoyl, trihalomethyl, aryl, aralkyl, hetero, thio, thioalkyl, alkylmercapto, hydroxy, hydroxyalkyl, alkoxy, amino, aminoalkyl, alkylamino, sulfinyl, sulfonyl or methylenedioxy,
n is an integer from 0 to 3 inclusive, and
$R_2$ and $R_3$ are independently hydrogen, alkyl, alkenyl, alkinyl, hydroxy, hydroxyalkyl, alkoxy, halogen, amino, aminoalkyl, alkylamino, alkanoylamino, thio, thioalkyl, alkylmercapto, carboxy, carbalkoxy, alkylsulfinyl, alkylsulfonyl, arylsulfinyl, or arylsulfonyl, wherein the alkyl groups contain from 1 to 6 carbon atoms, the alkenyl and alkynyl groups contain from 2 to 6 carbon atoms, and the aryl groups contain from 6 to 10 carbon atoms. These compounds have anti-allergy activity.

8 Claims, No Drawings

PYRIDOTHIENOPYRIDAZINE ANTI-ALLERGY COMPOUNDS

This invention relates to new chemical compounds possessing valuable pharmaceutical activity. It particularly relates to pyridothienopyridazines possessing useful anti-allergy activity and having the structure

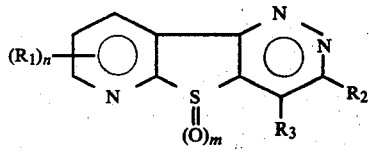

wherein
$R_1$ is alkyl, alkenyl, alkynyl, halogen, nitro, cyano, carboxy, carboxyalkyl, carbalkoxy, alkanoyl, trihalomethyl, aryl, aralkyl, hetero, thio, thioalkyl, alkylmercapto, hydroxy, hydroxyalkyl, alkoxy, amino, aminoalkyl, alkylamino, sulfinyl, sulfonyl or methylenedioxy,
m is an integer from 0 to 2 inclusive,
n is an integer from 0 to 3 inclusive, and
$R_2$ and $R_3$ are independently hydrogen, alkyl, alkenyl, alkinyl, hydroxy, hydroxyalkyl, alkoxy, halogen, amino, aminoalkyl, alkylamino, alkanoylamino, thio, thioalkyl, alkylmercapto, carboxy, carbalkoxy, alkylsulfinyl, alkylsulfonyl, arylsulfinyl, or arylsulfonyl.

The alkyl groups in alkyl per se and in hydroxyalkyl, alkoxy, thioalkyl, alkylmercapto, aminoalkyl, alkylamino, alkanoyl, carbalkoxy, aralkyl, alkylsulfinyl and alkylsulfonyl are either straight-chain or branched lower alkyl groups containing from 1 to 6 carbon atoms.

The alkenyl and alkynyl groups may be straight-chain or branched and contain from 2 to 6 carbon atoms.

The aryl groups contain from 6 to 10 carbon atoms and include phenyl, α-naphthyl, and β-naphthyl. These groups as well as the heterocyclic groups, may carry substituents such as alkyl, alkenyl, alkynyl, hydroxy, alkoxy, thio, alkylmercapto, amino, alkylamino, cyano, carboxy, carbalkoxy, sulfinyl, sulfonyl, trifluoromethyl, methylenedioxy, halogen, and nitro.

The halogen substituents are preferably chlorine, bromine and trifluoromethyl.

Suitable acid addition salts include salts of inorganic acids such as hydrochloric, sulfuric and phosphoric and organic acids such as acetic, lactic, benzoic, nicotinic, malic, succinic, tartaric, citric, mandelic and the like.

Suitable basic salts include salts of alkali and alkaline earth metals, iron, and amines.

The preferred compounds of the present invention are those wherein n is 1, $R_1$ is lower alkyl, $R_2$ is carboxy or carbalkoxy, and $R_3$ is hydroxy or alkoxy.

The compounds of the present invention may be prepared by the following sequence of reactions:

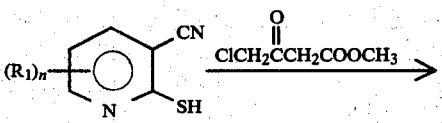

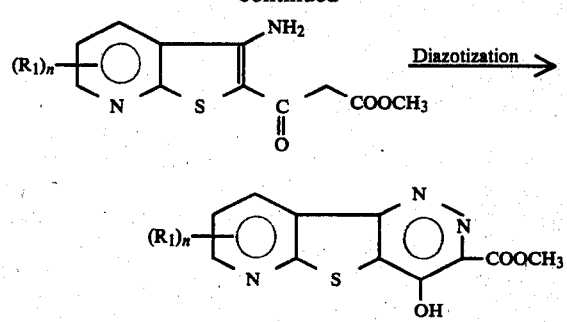

The $R_2$ carbomethoxy group can be readily saponified to a free carboxylic acid and, if desired, the carboxyl group removed by heating.

The $R_3$ hydroxy group can be readily converted into other groups by known chemical reactions.

It is to be understood that certain compounds of this invention may have asymmetric carbon atoms and thus may exist in racemic or optically active forms. These different forms are considered to be within the scope of the present invention.

The invention will be made clearer from the examples which follow. These examples are given by way of illustration and are not to be considered as limiting.

EXAMPLE 1

3-Carbomethoxy-4-Hydroxy-7-Methyl-Pyrido-[3',2'-4,5]-Thieno[3,2-C]Pyridazine

To a solution of 6 g (0.022 mol) of 3-amino-2-carbomethoxyacetyl-6-methyl-thieno[2,3-b]pyridine in 1.8 ml acetic acid and 180 ml dioxane was slowly added 4.8 g (4.2 ml, 0.041 mol) of isoamylnitrite and stirring continued for 24 hours. It was then poured on ice-water, filtered and washed with water. The crude product was crystallized from DMSO/H₂O to give 4.0 g (64%) of 3-carbomethoxy-4-hydroxy-7-methylpyrido[3',2':4,5]-thieno[3,2-c]pyridazine; m.p., 265°–268° C.

EXAMPLE 2

3-Carboxy-4-Hydroxy-7-Methyl-Pyrido[3',2':4,5]-Thieno[3,2-C]Pyridazine

A mixture of 4 g (0.015 mol) of 3-carbomethoxy-4-hydroxy-7-methylpyrido[3',2':4,5]thieno[3,2-C]pyridazine in 60 ml of 3% NaOH solution was stirred at room temperature for 2 hours. It was then diluted with water, treated with charcoal and filtered. It was acidified with acetic acid and filtered. Crystallization of the crude product from 3% NaOH/HOAC gave 2 g (53%) of 3-carboxy-4-hydroxy-7-methylpyrido[3',2':4,5]-thieno[3,2-C]pyridazine, m.p.>300° C.

EXAMPLE 3

4-Hydroxy-7-Methyl-Pyrido-[3',2':4,5]-Thieno-[3,2-C]-Pyridazine

A mixture of 2.4 g (0.009 mol) of 3-carboxy-4-hydroxy-7-methylpyrido[3',2':4,5]-thieno[3,2-C]pyridazine in 70 ml of Dowtherm-A was stirred at 225° C. for 30 minutes. It was cooled, diluted with hexane and filtered. The crude product was crystallized by 5% NaOH/HOAC giving 1.3 g (65%) of 4-hydroxy-7-methylpyrido[3',2':4,5]thieno[3,2-C]pyridazine; m.p.>300° C.

EXAMPLE 4

4-Hydroxy-7-Methyl Pyrido[3',2':4,5]Thieno-[3,2-C]Pyridazine-3-Carboxylate Sodium Salt To a solution of 370 mg (0.016 mol) of sodium in 250 ml ethanol was added 4.2 g (0.016 mol) of 3-carbethoxy-4-hydroxy-7-methyl-pyrido[3',2':4,5]thieno[3,2-C]pyridazine and stirring was continued for two hours. Solvent was then removed, the residue was diluted with 30 ml water and the product was filtered giving 3.3 g of the sodium salt of 3-carboxy-4-hydroxy-7-methyl pyrido[3',2':4,5]thieno[3,2-C]pyridazine; m.p.>300° C.

EXAMPLE 5

3-Carbethoxy-4-Ethoxy-7-Methyl-Pyrido[3',2':4,5]-Thieno[3,2-C]Pyridazine

To a mixture of 3.3 g (0.013 mol) of 3-carbomethoxy-4-hydroxy-7-methyl-pyrido[3',2':4,5]thieno[3,2-C]pyridazine, 3.8 g potassium bicarbonate, in 90 ml of anhydrous DMF was slowly added 9 ml of ethyl bromide and stirring was continued at 60°–70° C. for 3 hours. The solvent was then removed, the residue was diluted with water and filtered to give 3.4 g of crude product. Crystallization from EtOAc-hexane gave 1.8 g (46%) of pure 3-carbethoxy-4-ethoxy-7-methyl pyrido[3',2':4,5]thieno[3,2-C]pyridazine; m.p. 158°–160° C.

EXAMPLE 6

Step A

3-Amino-2-[2-(4-chlorophenylsulfonyl)-acetyl]-6-methyl-thieno[2,3-b]-pyridine To a mixture of 5.4 g (0.1 mol) of sodium methoxide and 7.5 g (0.05 mol) of 2-mercapto-3-cyano-6-methyl pyridine in 100 ml methanol was slowly added 13.3 g (0.05 mol) of 3-chloro-1-(4-chloro-phenylsulfonyl)-2-propanone. The reaction mixture was refluxed for 7 hours. It was then cooled, diluted with water and filtered to give 15.5 g of crude product which was crystallized from acetonitrile to give 12.8 g of pure product, m.p. 265°–7° C.

Step B

3-(4-Chlorophenylsulfonyl)-4-hydroxy-7-methyl-pyrido[3',2':4,5]thieno[3,2-c]pyridazine To a mixture of 4 g of 3-amino-2[2-(4-chlorophenylsulfonyl)-acetyl]-6-methyl-thieno-[2,3-b]pyridine in 100 ml of 5% hydrochloric acid was slowly added 2.1 g sodium nitrite in 20 ml water and stirring was continued for 24 hours. To this mixture was then added a solution of 1.8 g of sodium nitrite in 30 ml of 5% hydrochloric acid and stirring was continued for another 24 hours. The reaction was diluted with water and filtered to give crude product which was crystallized from DMSO, m.p.>300° C.

Following the procedures of the above examples, the following additional compounds can be prepared:

3-Carboxy-4-hydroxy-pyrido[3',2':4,5]thieno[3,2-c]pyridazine
3-Cyano-4-hydroxy-7-phenyl-pyrido[3',2':4,5]thieno[3,2-c]pyridazine
3-Carboxy-4-chloro-7,9-dimethyl-pyrido[3',2':4,5]thieno[3,2-c]pyridazine
3-Carbamido-4-chloro-7,9-diphenyl-pyrido[3',2':4,5]thieno[3,2-c]pyridazine
3-Carboxy-4-amino-7-methyl-9-phenyl-pyrido[3',2':4,5]thieno[3,2-c]pyridazine
3-Carboxy-4-hydroxy-7-methyl-9-chloro-pyrido[3',2':4,5]thieno[3,2-c]pyridazine
3-Carbamido-4-hydroxy-7,8-dimethyl-pyrido[3',2':4,5]-thieno[3,2-c]pyridazine
3-Carboxy-4-hydroxy-7,8-diphenyl-pyrido[3',2':4,5]-thieno[3,2-c]pyridazine
3-Acetyl-4-ethoxy-7-methyl-8-phenyl-pyrido[3',2':4,5]-thieno[3,2-c]pyridazine
3-Carboxy-4-hydroxy-7-methyl-8-cyano-pyrido[3',2':4,5]thieno[3,2-c]pyridazine
3-Sulfonic acid-4-hydroxy-7-methyl-8-trifluoromethyl-pyrido[3',2':4,5]thieno[3,2-c]pyridazine
3-Tetrazino-4-hydroxy-7-phenyl-8-chloro-pyrido[3',2':4,5]thieno[3,2-c]pyridazine
3-Sulfonic acid-4-hydroxy-7-ethyl-8-nitro-pyrido[3',2':4,5]thieno[3,2-c]pyridazine
3,8-Dicarboxy-2-hydroxy-7-phenyl-pyrido[3',2':4,5]-thieno[3,2-c]pyridazine The compounds of the present invention show strong activity as inhibitors of wheal formation in the passive cutaneous anaphylaxis (PCA) screen and as inhibitors of histamine release from passively sensitized rat mast cells (RMC), making them useful in the treatment of allergy. The compounds exhibit $ED_{50}$ values of from 1.0 to 50.0 mg/kg on oral administration in the PCA screen and $I_{50}$ values of from 1 to 100 μm in the RMC screen. The compounds may be administered orally or parenterally in the treatment of allergies and related conditions, and it will be within the skill of the practitioner to determine the exact amount to be administered and the mode of administration.

We claim:

1. A compound of the formula wherein
$R_1$ is alkyl, alkenyl, alkynyl, halo, nitro, cyano, carboxy, carboxyalkyl, carbalkoxy, alkanoyl, trihalomethyl, aryl, aralkyl, alkylmercapto, hydroxy, hydroxyalkyl, alkoxy, amino, aminoalkyl, alkylamino, or methylenedioxy,
m is an integer from 0 to 2 inclusive,
n is an integer from 0 to 3 inclusive, and
$R_2$ and $R_3$ are independently hydrogen, alkyl, alkenyl, alkinyl, hydroxy, hydroxyalkyl, alkoxy, halogen, amino, aminoalkyl, alkylamino, alkanoylamino, alkylmercapto, carboxy, carbalkoxy, alkylsulfinyl, alkylsulfonyl, arylsulfinyl, or arylsulfonyl, wherein in $R_1$, $R_2$ and $R_3$ the alkyl groups contain from 1 to 6 the alkyl groups contain from 1 to 6 carbon atoms, the alkenyl and alkynyl groups contain from 2 to 6 carbon atoms, and the aryl groups contain from 6 to 10 carbon atoms.

2. A compound of the formula

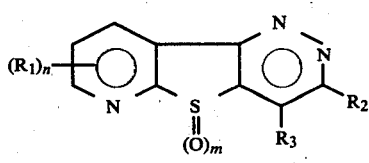

wherein
m is an integer from 0 to 2 inclusive,
n is an integer from 0 to 3 inclusive,
$R_1$ is alkyl, alkenyl, alkynyl, halo, nitro, cyano, carboxy, carboxyalkyl, alkanoyl, trihalomethyl, aryl, aralkyl, alkylmercapto, hydroxy, hydroxyalkyl, alkoxy, amino, aminoalkyl, or alkylamino, and
$R_2$ and $R_3$ are independently hydrogen, alkyl, alkenyl, alkynyl, hydroxy, hydroxyalkyl, alkoxy, halogen, amino, aminoalkyl, alkylamino, alkanoylamino, alkylmercapto, carboxy, carbalkoxy, alkylsulfinyl, alkylsulfonyl, arylsulfinyl, or arylsulfonyl, wherein in $R_1$, $R_2$ and $R_3$ the alkyl groups contain from 1 to 6 carbon atoms, the alkenyl and alkynyl groups contain from 2 to 6 carbon atoms, and the aryl groups contain from 6 to 10 carbon atoms.

3. A compound of the formula

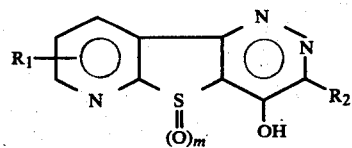

wherein
m is an integer from 0 to 2 inclusive,
$R_1$ is alkyl containing 1 to 6 carbon atoms, and
$R_2$ is hydrogen, carboxy or carbalkoxy.

4. A compound according to claim 3 wherein $R_1$ is methyl.

5. A compound according to claim 4 wherein $R_2$ is hydrogen.

6. A compound according to claim 4 wherein $R_2$ is carboxy.

7. A compound according to claim 4 wherein $R_2$ is carbalkoxy.

8. A compound according to claim 4 wherein $R_2$ is carbethoxy.

* * * * *